United States Patent

Huprich et al.

Patent Number: 5,942,239
Date of Patent: Aug. 24, 1999

[54] METHOD AND COMPOSITION FOR COATING WOUND OR PROTECTING ANIMAL SKIN

[75] Inventors: Carl A. Huprich, Robertsdale, Ala.; Leo L. Timms, Ames, Iowa; Thomas C. Hemling, Lake Winnebago, Mo.

[73] Assignee: Iowa State University Research Foundation, Inc., Ames, Iowa

[*] Notice: This patent is subject to a terminal disclaimer.

[21] Appl. No.: 08/799,869

[22] Filed: Feb. 14, 1997

Related U.S. Application Data

[63] Continuation-in-part of application No. 08/644,009, May 9, 1996.

[51] Int. Cl.⁶ .............................. A61K 6/00; A61K 7/00; A61K 31/74
[52] U.S. Cl. ........................ 424/401; 424/78.03
[58] Field of Search .................. 424/78.03, 401

[56] References Cited

U.S. PATENT DOCUMENTS

5,192,536  3/1993  Huprich .
5,413,780  5/1995  Huprich .............................. 424/78.02

OTHER PUBLICATIONS

Hackh's Chemical Dictionary, 4th Edition, 1969, p. 89.

Primary Examiner—Thurman K. Page
Assistant Examiner—Sharon Howard
Attorney, Agent, or Firm—Zarley,McKee,Thomte,Voorhee&Sease

[57] ABSTRACT

A polyether polyurethane/benzoin skin protectant is described which further includes a fast drying solvent. The skin protectant may optionally include a germicidal agent and/or a dye for better visualization of the protectant on the skin. The skin protectant provides a dry film that is elastic, vapor permeable, water proof, dirt proof, insect proof, aerobic bacteriostatic, and adheres well under environmental conditions. Apparent application viscosity can be adjusted as required for specific needs.

21 Claims, 1 Drawing Sheet

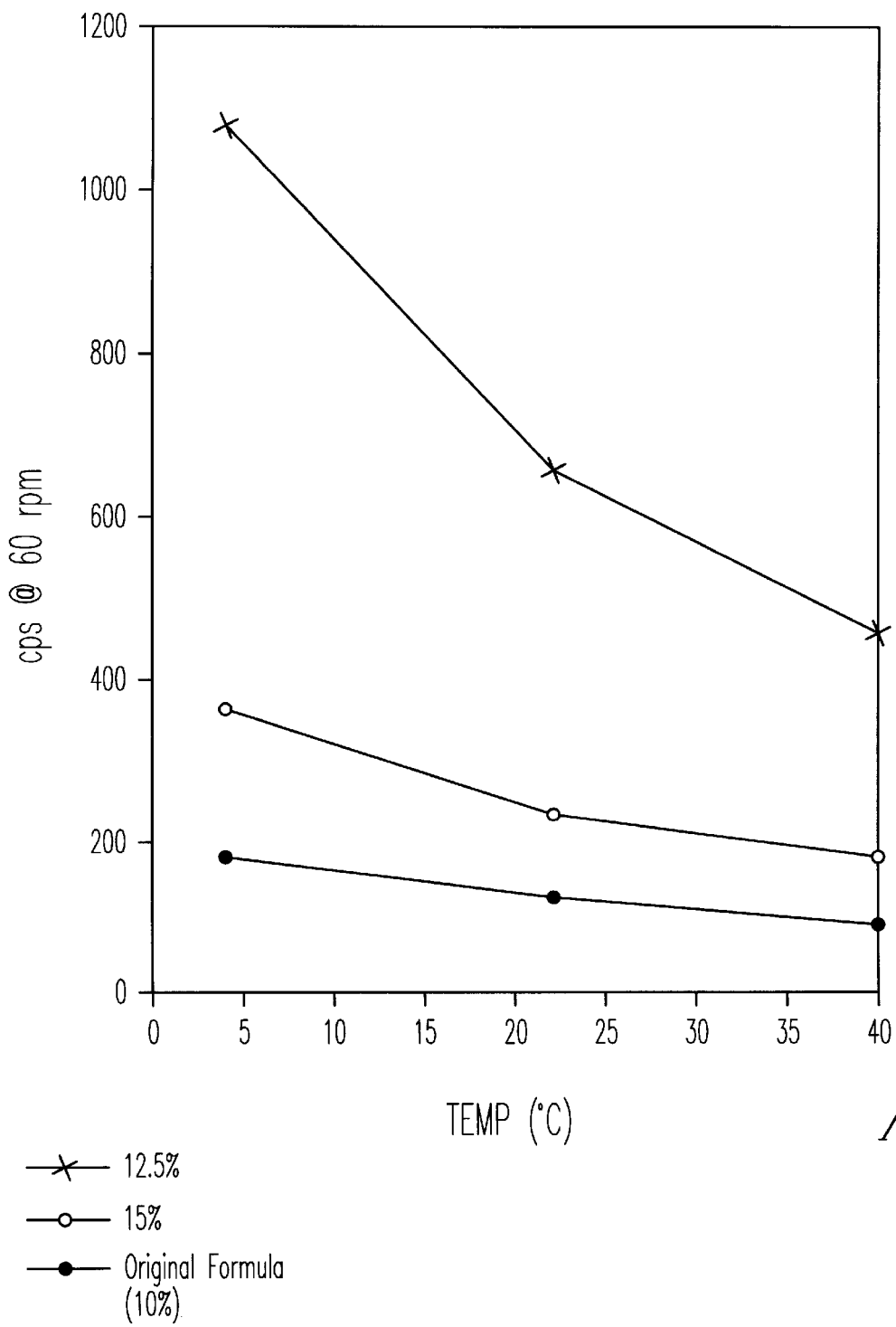

METHOD AND COMPOSITION FOR COATING WOUND OR PROTECTING ANIMAL SKIN

CROSS-REFERENCE TO RELATED APPLICATIONS

This application is a continuation-in-part application of Ser. No. 08/644,009 filed May 9, 1996.

BACKGROUND OF THE INVENTION

Protecting wounds and animal skin from damage by environment, abrasion, wind, dirt, water, insect bites, etc. has been difficult. Most treatments are ineffective or require replacement frequently and may aggravate the conditions present. U.S. Pat. No. 5,192,536, issued to Huprich, covered a successful method and composition for coating a wound with polyether polyurethane. Polyether polyurethane dissolved in tetrahydrofuran provides a solution that can be applied to animal skin and dries rapidly to an elastic film that is vapor permeable, waterproof, wind proof, dirt proof, insect proof, and presents a barrier to bacteria. This film protects the skin from further damage during the healing process or exposure. This composition is useful and overcomes most of the problems inherent with conventional treatments.

Adhesion time is a factor which affects the efficacy of skin protectants. It is also important that the method of application provide complete rather than partial coverage of the area sought to be protected.

The invention of the parent case (Ser. No. 08/644,009) describes a polyether polyurethane composition dissolved in tetrahydrofuran (THF) which includes benzoin film or benzoin gum (hereinafter referred to as "benzoin/THF skin protectant"). The benzoin gum presents a patentable improvement over prior art skin protectants. First, the benzoin gum almost doubles the adhesion time of the polyether polyurethane composition to the affected skin area. Further, the benzoin gum converts a previously spreadable solution of polyether polyurethane to a composition suitable for dipping body extensions and limbs, thereby improving the ability of the composition to coat affected skin areas completely. An example of a preferred benzoin/THF skin protectant in accordance with the parent application is set forth as follows:

100 parts tetrahydrofuran
10 parts polyether polyurethane
5 parts benzoin gum

The amount of benzoin included in the composition can be adjusted to allow for more effective coverage of the desired surface area as necessary. The composition can be applied by a variety of methods including dipping, spraying, spreading, and wiping.

The benzoin/THF skin protectant may be used for a variety of skin protection purposes. It is especially useful as a teat dip for the prevention of mastitis. Up to 40–50% of intramammary infections are contracted during a cow's dry or non-lactating period, with the greatest percentages of these infections occurring during the first and last two weeks of the dry period. At these times, the mammary gland is in a transitional state: immunological factors are preoccupied or suppressed, milk is no longer being flushed from the gland, and increased mammary pressure distends the teat, thus allowing for easier bacterial penetration through the streak canal. The primary goal for mastitis control during the dry period is to minimize bacterial exposure on teat ends. Due to its long adhesion time and coverage, the benzoin skin protectant is useful for the prevention of mastitis during the dry cow period.

It would also be desirable to incorporate a germicide in the benzoin/THF skin protectant in order to further deter bacterial infection. Anti-mastitis compositions which include a germicide have previously been developed. For example, U.S. Pat. No. 4,891,216 discloses the incorporation of a chlorous acid/chlorine dioxide system. U.S. Pat. No. 5,529,770 discloses the incorporation of iodine as a germicide in an aqueous lactating cow barrier composition. However, both of the systems described in these patents are aqueous. The benzoin/THF skin protectant of the parent application presents unique formulation problems since it is not an aqueous system.

For example, iodine crystals will readily dissolve in tetrahydrofuran (THF) when added to the benzoin/THF skin protectant. However, upon standing, the composition shows a decrease in pH and a color change, indicating a chemical reaction between the iodine and the other ingredients of the formulation. Also, attempts to dissolve povidone iodine powder into the benzoin formulation have been unsuccessful.

It has now been discovered that certain germicidal agents can be added to the previously described benzoin/THF skin protectant to produce a stable, effective, germicidal skin protectant.

It has also been discovered that dyes can be added to the benzoin/THF skin protectant to make it easier to visualize on the skin area where it has been applied. Further, other solvents may be substituted for the THF which may in some instances significantly decrease the cost of manufacturing the benzoin skin protectant.

It is therefore a primary objective of the present invention to provide a highly adhesive, benzoin skin protectant composition which is also germicidal.

It is a further objective of the present invention to provide a germicidal benzoin skin protectant which is stable.

It is a further objective of the present invention to provide a germicidal benzoin skin protectant which is not harmful to animal skin.

It is a further objective of the present invention to provide a benzoin skin protectant which includes an indicator dye.

It is a further objective of the present invention to provide a germicidal benzoin skin protectant which is economical to manufacture.

These and other objectives will become clear from the following description of the invention.

SUMMARY OF THE INVENTION

The present invention generally relates to a skin protectant comprised of benzoin, polyether polyurethane and a solvent. The solvent may be tetrahydrofuran or other compatible solvents which also provide the advantageous properties of tetrahydrofuran. The skin protectant dries rapidly to an elastic film that is vapor permeable, water proof, wind proof, dirt proof, insect proof, and presents a barrier to bacteria. The film protects the skin from further damage during the healing process or exposure.

The invention further includes the incorporation of various germicides into the skin protectant. The germicidal compositions are stable and are effective against a variety of infectious organisms commonly associated with mastitis and other types of skin infections, including *Staph. aureous*. The skin protectant may also contain a dye to improve the visualization of the skin protectant on the skin.

DESCRIPTION OF THE DRAWING

FIG. 1 is a graph illustrating the effect of temperature on the viscosity of different formulations of the benzoin/THF skin protectant.

DETAILED DESCRIPTION OF THE INVENTION

As set forth above, all formulations within the scope of the present germicidal skin protectants includes polyether polyurethane, and benzoin gum (hereinafter collectively referred to as the "film-forming component"). The formulation also contains a solvent. While the parent application describes the solvent as being tetrahydrofuran, it has now been discovered that other solvents may be substituted for the tetrahydrofuran to form a skin protectant which performs comparatively to the benzoin/THF skin protectant. The primary advantage to the substitution is that several of the solvents used are significantly less expensive than THF, thus lowering the manufacturing costs of the skin protectant.

The film forming component comprises from about 5% to about 50% by weight of the overall concentration of the skin protectant. The preferred range is from about 5% to about 30% by weight. As set forth in the parent application, a preferred formulation comprises about 8% polyether polyurethane and about 5% benzoin gum.

The other required ingredient in the skin protectant is a solvent. Once the percentages of film-forming component and other optional ingredients are determined, the solvent comprises the remaining portion of the skin protectant formulation.

The viscosity of the skin protectant should be from about 50 cPs to 2000 cPs at 25° C. The preferred range is 100 to 1500 and the most preferred range is from 140 to 800 cPs. The following formulations were tested for viscosity:

TABLE I

| | Formula Name | | |
|---|---|---|---|
| | 10% | 12.5% | 15% |
| Estane 5714 | 10 parts | 12.5 parts | 15 parts |
| Benzoin Resinoid | 5 parts | 5 parts | 5 parts |
| THF | 100 parts | 100 parts | 100 parts |

The viscosities of the formulations in Table I at varying temperatures were determined using a Brookfield viscometer at 60 rpm using spindle #3. The results are set forth in Table II and a graphic representation is shown in FIG. 1.

TABLE II

| | % Polyurethane | | |
|---|---|---|---|
| Temp. ° C. | 12½% | 15% | 10% |
| 4 | 378 | 1086 | 180 |
| 22 | 236 | 662 | 126 |
| 40 | 180 | 462 | 90 |

It has also been found that other solvents may be substituted for tetrahydrofuran (THF) in the benzoin/THF skin protectant. Acceptable solvents are those which provide stable skin protectant compositions which also provide a drying time of less than about 20 minutes following application to the skin area sought to be treated and which exhibit low toxicity. "Dry" is defined as being dry to the touch. The most preferred solvents are those having a drying time of less than about 10 minutes.

Suitable solvents include tetrahydrofuran (THF) and cyclohexanone. Cosolvents may also be included and include: methylethyl ketone (MEK), toluene, acetone, methanol, ethanol, propanol, isopropanol, and propylene glycol. Further, combinations of the solvents and cosolvents may be used. The alcohols are the preferred cosolvents based on rapid evaporation rate and their ability to lower manufacturing costs. For instance, THF currently sells for about $1.60/lb., whereas isopropanol, for example, sells for about $0.30/lb.

A germicide may optionally be included in the skin protectant. Formulating the benzoin skin protectant with a germicidal agent has proven to be difficult, especially since the composition is film-forming rather than aqueous. It has surprisingly been discovered that chlorhexidine diacetate and other types of germicides can be incorporated into the benzoin skin protectant to form a stable, effective, germicidal skin protectant.

There are several germicides which have been found to be compatible with the benzoin skin protectant of the parent application. For purposes of this application, a germicide is "compatible" with the benzoin skin protectant if the resulting formulation is physically and chemically stable at ambient temperatures. Compatible germicides include chlorhexidine diacetate and chemically related germicides, including polyhexamethylene biguanide. Other germicides which have been tested and found compatible with the benzoin skin protectant include:

a) linear or branched fatty acid germicides, such as octanoic acid, nonanoic acid, and decanoic acid; and
b) quaternary ammonium compounds, including salts of alkyl dimethylbenzyl ammonium, Barquat MB-80™ (Lonza™), dialkyl dimethyl ammonium compounds (Bardac 208M™, Lonza™, Inc.), and benzthonium (Hyamine 1622™, Lonza™, Inc.). Combinations of these germicides may also be used, with the exception that fatty acid germicides may not be compatible with the quaternary ammonium germicides.

The germicide(s) should comprise from about 0.05% to about 2% by weight of the overall skin protectant formulation. The preferred level is from about 0.1% to about 1.0% by weight.

Dyes may optionally be incorporated into the benzoin skin protectant to improve the visualization of the barrier film on the skin area being treated. Acceptable dyes include those that are soluble or dispersible in the benzoin skin protectant. The preferred dyes provide easy visualization of the barrier film from distances up to at least 20 feet and can be used at relatively low concentrations in the composition. The dye(s) should comprise from about 0.001% to about 0.2% be weight of the skin protectant. The preferred amount is about 0.05%.

Dyes giving bright red or pink colors are usually the easiest to visualize at great distances, but other colors may also be acceptable. Suitable dyes include: Rhodamine B (D&C Red 19), solvent yellow 43 (Keyplast F1 Yellow R™, CAS No. 19125-99-6, fluoro yellow naphthalic acid imide, Keystone Analine Corp.), Keyplast yellow 2GH™ (Keystone Analine Corp.), FD&C red 3, FD&C red 22, FD&C red 28, and FD&C red 39.

Some of the listed dyes may not be compatible with all of the germicides set forth above. Specifically, dyes which contain acid functional groups, such as carboxylic acids or sulfonic acid groups or the corresponding salts are not likely to be compatible with quaternary germicides or chlorhexidine. FD&C 19 is an example of an acid dye that is compatible with the skin protectant which does not contain a germicide, but is not compatible when quaternary germicides of chlorhexidine are included. It is, however, compatible with fatty acid germicides. The following dyes are compatible with skin protectant formulations which incorporate the quaternary or chlorhexidine germicides: FD&C Green 6, Orange 5, Orange 10, Orange 17, Red 17, Red 21, Red 27, Red 31, Violet 2, Yellow 7, and Yellow 11.

The present invention further contemplates that other ingredients such as fillers, moisturizers, perfumes, and viscosity modifiers, such as thickeners and thixotropic agents, may be added to the skin protectant formula. The only requirement is that the additives be compatible with the other ingredients of the composition. The selection of compatible additives can be readily ascertained by those of ordinary skill in the art. The levels of these minors are generally not more than 0.001% to 2% by weight.

The following examples are provided to illustrate, but not limit, the present invention in any manner.

EXAMPLE 1

Evaluation of 10% Benzoin/THF Skin Protectant for the Prevention of Mastitis During the Dry Period The overall objective of this research was to develop a barrier type teat dip product which could 1) persist for 3–7 days on teat ends of dry cows; 2) prevent intramammary infections (IMI); and 3) not harm teat tissue. The objective of this presented research was to evaluate a novel barrier teat dip for preventing IMI under natural exposure conditions.

Materials and Methods

A natural exposure field trial was conducted from November 1995–November 1996 using the 10% benzoin/THF skin protectant formulation shown in Table I. This formulation was shown to persist >3 days on 98% of dipped quarters of dry cows in preliminary studies. All dry cows and freshening heifers at the Iowa State University Dairy Farm were included in the trial. The trial was a randomized half udder design with either right or left quarters dipped while the others served as controls. All cows were dry treated. Cows were only dipped once at dry off following dry cow treatment administration. Cows and heifers were dipped starting approximately 10 days prepartum and were redipped as needed until parturition. Dip persistency was evaluated daily on all cows. Duplicate aseptic quarter milk samples were taken at 3 days pre-dry off, dry off, calving, and 3 days postpartum and frozen until subsequent bacteriological analysis. All samples were initially cultured on blood agar for 24–48 hrs at 37° C. Isolates were differentiated using gram staining, catalase and coagulase testings, and CAMP and EMB agar plates.

Results

New IMI at calving are shown in Table III. A total of 190 cows and 756 quarters completed the trial (66 heifers, 264 quarters, 124 cows, 492 quarters). Dipped quarters of heifers show a 20, 40 and 50% reduction in total, major pathogen, and environmental streptococcal (ES) IMI, with no significant reduction in coagulase negative staphylococcal (CNS) or gram negative IMI. Dipped quarters of cows showed a 53, 52, 68, and 43% reduction in total, major pathogen, ES, and CNS IMI with no reduction in gram negative IMI. Combining data from both groups shows an overall reduction of 37, 48, 63, and 28% of total, major pathogen, ES, and CNS IMI in dipped quarters as compared to controls. Two problems during the late spring–summer including switching of transition cow and heifer lots (May–June, 15/18 gram negatives occurred, dip unable to dry before exposed to moisture) and decreased product viscosity (persistency) above 65° F. were encountered and may explain the limited reduction in gram negative IMI and lower reductions in IMI in heifers as compared to cows.

Summary and Implications

Dipping of cows at dry off and cows and heifers 10 day prepartum until calving with an experimental barrier teat dip product resulted in a 20, 40, and 50% reduction of total, major pathogen, and environmental streptococcal IMI at calving in heifers and a 53, 52, 68, and 43% reduction in total, major pathogen, environmental streptococcal, and coagulase negative staphylococcal IMI at calving in cows. This novel persistent barrier teat dip significantly reduced dry period and calving IMI, and had no effect on teat tissue. This dip may provide an alternative to dry cow therapy in low SCC cows at dry off.

TABLE III

| | | | | | | TOTAL INFECTED | |
|---|---|---|---|---|---|---|---|
| | NG | CNS | SA | ES | G− | w/o CNS | w/CNS |
| Heifers n = 66; 264 quarters; | | | | | | | |
| Dipped | 102 | 21 | 1 | 4 | 3 | 9 | 30 |
| No Dip | 95 | 22 | 2 | 10 | 3 | 15 | 37 |
| Cows n = 124; 492 quarters; | | | | | | | |
| Dipped | 213 | 20 | 1 | 7 | 5 | 13 | 33 |
| No Dip | 184 | 35 | 0 | 22 | 5 | 27 | 62 |
| Totals n = 190; 756 quarters; | | | | | | | |
| Dipped | 315 | 41 | 2 | 12 | 8 | 22 | 63 |
| No Dip | 279 | 57 | 2 | 32 | 8 | 42 | 99 |

NG = uninfected;
CNS = coagulase negative staphylococcus;
SA = *Staph. aureus*;
ES = environmental streps;
G− = gram negatives

EXAMPLE 2

Stability of Solvents

Various solvents were tested for their ability to form stable skin protectants in combination with polyether polyurethane and benzoin in accordance with the present invention. The results are set forth in Table IV:

TABLE IV

| | Formula | | | | | | | | |
|---|---|---|---|---|---|---|---|---|---|
| | A | B | C | D | E | F | G | H | I |
| % THF | 80.15 | 75.15 | 70.15 | 80.15 | 75.15 | 70.15 | 80.15 | 75.15 | 70.15 |
| % Estane | 10.6 | 10.6 | 10.6 | 10.6 | 10.6 | 10.6 | 10.6 | 10.6 | 10.6 |
| % Benzoin | 4.25 | 4.25 | 4.25 | 4.25 | 4.25 | 4.25 | 4.25 | 4.25 | 4.25 |
| % Methanol | 5.0 | 10.0 | 15.0 | — | — | — | — | — | — |

TABLE IV-continued

|  | Formula | | | | | | | | |
| --- | --- | --- | --- | --- | --- | --- | --- | --- | --- |
|  | A | B | C | D | E | F | G | H | I |
| % Ethanol | — | — | — | 5.0 | 10.0 | 15.0 | — | — | — |
| % Isopropanol | — | — | — | — | — | — | 5.0 | 10.0 | 15.0 |
| Initial Stability | OK | OK | OK | OK | OK | OK | OK | OK | OK |
| Stability, 1 week at RT | OK | OK | OK | OK | OK | OK | OK | OK | OK |
| Stability, 1 week at 40° C. | OK | OK | OK | OK | OK | OK | OK | OK | OK |

The above example demonstrates that alcohols are compatible as solvents with the benzoin/THF skin protectant at ambient temperatures and at 40° C.

EXAMPLE 3

Stability of Dyes with the Skin Protectant

In the skin protectant which does not contain a germicide, the preferred dye is D&C Red 19 (Rhodamine B) at a concentration of 0.05%. Some problems have occurred in the product upon the addition of chlorhexidine acetate due to an apparent interaction between the dye and the germicide. In the interest of finding additional dyes that may be compatible with the compositions of this invention, a number of different red dyes were added to assess their solubility and visual characteristics. The following formula was used:

85.1% THF
10.6% Estane 5714
4.25% Benzoin Resinoid
0.05% Dye

The results are set forth in Table V:

TABLE V

| Dye | Solubility | Solution Appearance | Dry Appearance | Dry Color Intensity* |
| --- | --- | --- | --- | --- |
| FD&C Red 2 | Completely insoluble | — | — | — |
| FD&C Red 3 | OK | Florescent red/orange | Pink | 3 |
| FD&C Red 4 | Very slightly soluble | — | — | — |
| FD&C Red 40 | Completely insoluble | — | — | — |
| D&C Red 22 | OK | Florescent orange | Light Pink | 2 |
| D&C Red 28 | OK | Florescent orange/red | Pink | 3 |
| D&C Red 33 | Insoluble | — | — | — |
| D&C Red 39 | OK - dissolves quickly | Red/orange | Dull orange | 4 |
| D&C Red 19 | OK | Florescent red | Magenta | 5 |

*The dry color intensity is based on a scale from 0 to 5; 5 being the most intense using D&C Red 19 as a standard, and 0 being colorless.

The above example demonstrates that FD&C Red 3, D&C Red 22, D&C Red 28, D&C Red 39, and D&C Red 19 are compatible with the benzoin/THF skin protectant and have fair to excellent visual characteristics.

EXAMPLE 4

Stability and Microbiocidal Activity of Chlorhexidine Diacetate

Chlorhexidine Diacetate was added with stirring to a previously prepared solution of THF, polyether polyurethane, and benzoin resinoid in accordance with the present invention as set forth in Table VI. The solution was mixed at ambient temperature until the chlorhexidine was fully dissolved. Physical stability of the composition was tested at ambient temperature and at 40° C. The chlorhexidine diacetate composition showed no signs of instability.

The microbiocidal activity of the compositions was tested against *Staph. aureus* using a Modified AOAC Use-Dilution Method (*Official Methods of Analysis of the AOAC*, 15th ed. 1990, Chapter 6, Section 955.15—Disinfectants, Use-Dilution Method). The samples were tested undiluted against 10 porcelain carriers of the test organism. The exposure conditions were 10 minutes at ambient room temperature. The test neutralizer and subculture medium was AOAC Fluid Thioglycollate medium with 4% glycine, 2% Tween®80, and 0.07% lecithin.

As shown in Table VI, an increase in chlorhexidine diacetate concentration increases the antimicrobial activity of the benzoin skin protectant against *Staph. aureus*. Example A, without chlorhexidine, showed growth on 10 of 10 carriers.

TABLE VI

| Raw Material | A | B | C | D |
| --- | --- | --- | --- | --- |
| THF | 86.96 | 86.74 | 86.53 | 86.09 |
| Estane 5714 | 8.70 | 8.67 | 8.65 | 8.61 |
| Benzoin Resinoid | 4.35 | 4.34 | 4.33 | 4.30 |
| Chlorhexidine Diacetate | 0.00 | 0.25 | 0.50 | 1.00 |
| TOTAL | 100.00 | 100.00 | 100.01 | 100.00 |
| Use Dilution Test |  |  |  |  |
| No. of Carriers Positive: | 10/10 | 9/10 | 8.3*/10 | 6.5*/10 |

*Indicates Average of Multiple Trials

As shown above, other solvents may be substituted for THF in the benzoin/THF skin protectant which enables the composition to be manufactured for a lower cost. Further, dyes and germicides may also be incorporated in the composition to further improve its properties. It is therefore submitted that the present invention accomplishes at least all of its stated objectives.

What is claimed is:

1. A fast-drying skin protectant comprising:
    polyether polyurethane;
    benzoin gum; and a solvent selected from the group consisting of cyclohexanone, methylethyl ketone, toluene, acetone, methanol, ethanol, propanol, isopropanol, propylene, and combinations thereof.
2. A skin protectant according to claim 1 wherein the solvent dries in less than about 20 minutes.
3. A skin protectant according to claim 1 which further includes a germicidal agent.

4. A skin protectant according to claim 4 wherein the germicidal agent is selected form the group consisting of linear or branched fatty acids, polyhexamethylene biguanide, chlorhexidine diacetate and quaternary ammonium compounds.

5. A skin protectant according to claim 5 wherein the germicidal agent is chlorhexidine diacetate.

6. A skin protectant according to claim 1 which further includes a dye.

7. A skin protectant according to claim 7 wherein the dye is selected from the group consisting of FD&C Red 3, Red 22, Red 28, Red 39, and Red 19.

8. A skin protectant according to claim 4 further including a dye selected from the group consisting of FD&C Green 6, Orange 5, Orange 10, Orange 17, Red 17, Red 21, Red 31, Violet 2, Yellow 7, and Yellow 11.

9. A skin protectant according to claim 1 wherein the benzoin gum and the polyether polyurethane together comprise from about 5–50% by weight of the skin protectant.

10. A skin protectant according to claim 10 wherein the polyether polyurethane comprises about 10% by weight of the formulation.

11. A skin protectant according to claim 4 wherein the germicidal agent comprises from about 0.05–2.0% by weight of the skin protectant.

12. A skin protectant according to claim 7 wherein the dye comprises from about 0.001–0.2% by weight of the skin protectant.

13. A process for protecting animal skin comprising:

applying a skin protectant comprising from about 5–50% polyether polyurethane and benzoin gum dissolved in a fast drying solvent;

said solvent being selected from the group consisting of cyclohexanone, methylethyl ketone, toluene, acetone, methanol, ethanol, propanol, isopropanol, and propylene glycol.

14. A process for protecting animal skin according to claim 14 wherein the skin protectant further includes a germicidal agent.

15. A process for protecting animal skin according to claim 14 wherein the skin protectant further includes a dye.

16. A process for protecting animal skin according to claim 14 wherein the skin protectant is applied by dipping.

17. A process for making a skin protectant comprising:

dissolving from about 5–50% polyether polyrethane and benzoin gum in a fast drying solvent selected from the group consisting of cyclohexanone, methylethyl ketone, toluene, acetone, methanol, ethanol, propanol, isopropanol, and propylene glycol.

18. A process according to claim 18 wherein a germicidal agent is dissolved in the solvent.

19. A process according to claim 18 wherein a dye is dissolved in the solvent.

20. A process according to claim 19 wherein a dye is dissolved in the solvent.

21. a fast-drying skin protectant comprising:

polyether polyurethane;

benzoin gum;

tetrahydrofuran; and a germicidal agent.

* * * * *

UNITED STATES PATENT AND TRADEMARK OFFICE
CERTIFICATE OF CORRECTION

PATENT NO. : 5,942,239
DATED : August 24, 1999
INVENTOR(S) : Huprich et al.

It is certified that error appears in the above-identified patent and that said Letters Patent is hereby corrected as shown below:

Claim 4, Column 9, line 1 delete [4] and substitute --3--.

Claim 5, Column 9, line 6 delete [5] and substitute --4--

Claim 7, Column 9, line 10 delete [7] and substitute --6--.

Claim 8, Column 9, line 13 delete [4] and substitute --3--.

Claim 10, Column 9, line 20 delete [10] and substitute --9--.

Claim 11, Column 9, line 23 delete [4] and substitute --3--.

Claim 12, Column 9, line 26 delete [7] and substitute --6--.

Claim 14, Column 10, line 6, delete [14] and substitute --13--.

UNITED STATES PATENT AND TRADEMARK OFFICE
CERTIFICATE OF CORRECTION

PATENT NO. : 5,942,239
DATED : August 24, 1999
INVENTOR(S) : Huprich et al.

It is certified that error appears in the above-identified patent and that said Letters Patent is hereby corrected as shown below:

Claim 15, column 10, line 9, delete [14] and substitute --13--.

Claim 16, column 10, line 11, delete [14] and substitute --13--.

Claim 18, column 10, line 19, delete [18] and substitute --17--.

Claim 19, column 10, line 21, delete [18] and substitute --17--.

Claim 20, column 10, line 23, delete [19] and substitute --18--.

Signed and Sealed this

Eighteenth Day of January, 2000

Attest:

Q. TODD DICKINSON

*Attesting Officer*    *Commissioner of Patents and Trademarks*